US006243095B1

(12) United States Patent
Shile et al.

(10) Patent No.: US 6,243,095 B1
(45) Date of Patent: Jun. 5, 2001

(54) NAVIGATION AND DISPLAY SYSTEM FOR DIGITAL RADIOGRAPHS

(76) Inventors: Peter E. Shile, 581 Purdue Ave., St. Louis; Vivin Ramamurthy, 6418 Enright Ave., University City, both of MO (US) 63130; Tatsuya Fujii, 7-51-5 Okusawa Setagaya, Tokyo 158 (JP)

( * ) Notice: Subject to any disclaimer, the term of this patent is extended or adjusted under 35 U.S.C. 154(b) by 0 days.

(21) Appl. No.: 08/908,546

(22) Filed: Aug. 7, 1997

Related U.S. Application Data

(63) Continuation of application No. 08/761,075, filed on Dec. 5, 1996.

(51) Int. Cl.[7] ....................................................... G06K 9/00
(52) U.S. Cl. ........................................... 345/357; 345/349
(58) Field of Search .................................... 345/357–356, 345/326, 327, 328, 329, 330, 331, 332, 333, 334, 335, 336, 337, 338, 339, 340, 350, 342, 351–352, 358, 157, 168, 162, 163, 161, 146, 145

(56) References Cited

U.S. PATENT DOCUMENTS

| 5,081,656 | * | 1/1992 | Baker et al. | 378/21 |
| 5,199,054 | * | 3/1993 | Adams et al. | 378/21 |
| 5,483,961 | * | 1/1996 | Kelly et al. | 128/653.1 |
| 5,488,952 | * | 2/1996 | Schoolman | 178/660.07 |
| 5,524,630 | * | 6/1996 | Crowley | 128/662.06 |
| 5,644,649 | * | 7/1997 | Schoeters et al. | 382/132 |
| 5,757,953 | * | 5/1998 | Jang | 382/132 |
| 5,774,599 | * | 6/1998 | Muka et al. | 382/254 |
| 5,787,886 | * | 8/1998 | Kelly et al. | 128/653.1 |

OTHER PUBLICATIONS

Freiherr, *Promise And Pitfalls Of Digital Mammography*, Diagnostic Imaging, Nov., 1996; pp. D13–DD16.
Freiherr, *Digital X–Ray Capture: Prelude To The Future*, Diagnostic Imaging, Nov., 1996, pp. D3–D6.
Beard et al., *A Radiography Workstation For Mammography: Preliminary Observations, Eyetracker Studies, And Design*, SPIE vol. 1446 Medical Imaging V:PACS Design and Evaluation (1991), pp. 289–296.
Fajardo, *New Detectors Boost Mammographic Accuracy*, Diagnostic Imaging, Nov., 1996, pp. D7–D9.

* cited by examiner

*Primary Examiner*—Steven Sax
(74) *Attorney, Agent, or Firm*—Polster, Lieder, Woodruff & Lucchesi

(57) ABSTRACT

A navigation and display system for digital radiographs comprises one high definition monitor (or two) for viewing digitally acquired images, a video buffer for storing the images to be displayed, and a control console having a graphical user interface (GUI) for controlling the display of the images on the high definition monitor. By storing all of the images to be displayed for a patient study in the video buffer, the images can be selectively displayed in a seemingly instantaneous manner. The GUI displays multiple icons, where each icon represents one of the radiographic images for the patient study in question. A cursor on the GUI is coupled to a mouse, where movement of the mouse controls the location of the cursor with respect to the icons, and hence the image(s) displayed on the high definition monitor. The icons are arranged such that hand movements required to control the mouse correspond to head and eye movements made by radiologists when viewing similar images on hard copy film. The images displayed can include the radiographic images as originally captured, as well as various renditions thereof including renditions of different spatial resolutions and images processed to highlight radiographic features of interest.

12 Claims, 7 Drawing Sheets

PATIENT EXAM ICON ARROW POINTS TO PRIOR CRANIO-CAUDAL IMAGE WHICH IS BEING DISPLAYED ON DIAGNOSTIC MONITOR AT MEDIUM RESOLUTION

PATIENT EXAM ICON ARROW POINTS TO CURRENT CRANIO-CAUDAL IMAGE WHICH IS BEING DISPLAYED ON DIAGNOSTIC MONITOR AT 100μ RESOLUTION

DIAGNOSTIC MONITOR: CURRENT AND PRIOR EXAM IMAGES VIEWED AT LOW RESOLUTION

DIAGNOSTIC MONITOR: CURRENT CRANIO-CAUDAL IMAGE VIEWED AT MEDIUM RESOLUTION

PATIENT EXAM ICON ARROW POINTS TO PRIOR CRANIO-CAUDAL IMAGE WHICH IS BEING DISPLAYED ON DIAGNOSTIC MONITOR AT MEDIUM RESOLUTION

DIAGNOSTIC MONITOR: PRIOR CRANIO-CAUDAL IMAGE VIEWED AT MEDIUM RESOLUTION

PATIENT EXAN ICON ARROW POINTS TO CURRENT OBLIQUE IMAGE WHICH IS BEING DISPLAYED ON DIAGNOSTIC MONITOR AT MEDIUM RESOLUTION

DIAGNOSTIC MONITOR: CURRENT OBLIQUE IMAGE VIEWED AT MEDIUM RESOLUTION

DIAGNOSTIC MONITOR: OLD OBLIQUE IMAGE VIEWED AT MEDIUM RESOLUTION

DIAGNOSTIC MONITOR: MASS PRESEMT ON CURRENT RIGHT CRANIO-CAUDAL VIEW AT MEDIUM RESOLUTION

DIAGNOSTIC MONITOR: MASS NOT PRESENT ON OLD RIGHT CRANIO-CAUDAL VIEW AT MEDIUM RESOLUTION

PATIENT EXAM ICAON GREEN BOX AND ARROW INDICATE SEGMENT OF NEW CRANIO-CAUDAL VIEW OF RIGHT BREAST BEING DISPLAYED ON DIAGNOSTIC MONITOR AT HIGH RESOLUTION

DIAGNOSTIC MONITOR: SEGMENT OF NEW CRANIO-CAUDAL VIEW OF RIGHT BREAST AT HIGH RESOLUTION

PATIENT EXAM ICON GREEN BOX AND
ARROW INDICATE SEGMENT OF NEW
CRANIO-CAUDAL VIEW OF LEFT BREAST
BEING DISPLAYED ON DIAGNOSTIC
MONITOR AT HIGH RESOLUTION

DIAGNOSTIC MONITOR: SEGMENT OF NEW
CRANIO-CAUDAL VIEW OF LEFT BREAST
AT HIGH RESOLUTION
POINTER IDENTIFIES MICROCALCIFICATIONS

NAVIGATION AND DISPLAY SYSTEM FOR DIGITAL RADIOGRAPHS

CROSS-REFERENCE TO RELATED APPLICATION

This application is a continuation of application Ser. No. 08/761,075, filed Dec. 5, 1996, pending the disclosure of which is incorporated herein by reference.

BACKGROUND OF THE INVENTION (1) Field of the Invention

The present invention relates to digitally acquired radiographs and, more particularly, to a high speed, high definition navigation and display system for digital mammograms.

(2) Description of the Related Art

The American Cancer Society estimates that 44,300 women will die this year from breast cancer, which is the leading cause of cancer-related deaths among women in the United States. X-ray mammography is the only proven tool capable of detecting this cancer in its early stages. Use of x-ray mammography doubled between 1987 and 1992, and conditions appear favorable for a continuing increase. Laurie L. Fajardo, M.D., *New Detectors Boost Mammographic Accuracy, Diagnostic Imaging,* November 1996, at D7.

Currently, mammograms are viewed on a multiviewer 100 (also known as a viewbox) as hard copy film, as shown in FIG. 1. Images from a current examination are hung on a lower level 102 of the multiviewer, and include a right cranial-caudal ("cc") view 104, a left cc view 106, a right oblique view 108, and a left oblique view 110. The same views from a prior comparison exam are hung on an upper level 112 of the multiviewer, and include a right cc view 104', a left cc view 106', a right oblique view 108', and a left oblique view 110'. In general, the images are viewed in a systematic order, and the current images are compared to the prior images to detect any changes. Thus, a mammographer reviewing the single patient study illustrated in FIG. 1 moves his head and eyes upwardly and downwardly to compare a set of views from the current and prior examinations, such as the right cc views 104, 104'. After conducting this comparison, the mammographer shifts his head and eyes from left to right to review the next view from the current examination, such as the left cc view 106, and then again shifts his head and eyes upwardly and downwardly to compare the left cc view 106 with the left cc view 106' from the prior examination. Other arrangements of the various views can be and sometimes are employed.

These reviews are ordinarily conducted first without magnification to identify abnormalities indicative of a cancer onset, including suspicious masses, and are then repeated with a magnifying lens to identify any clustered microcalcifications, another indicator of developing breast cancer. A typical multiviewer can hold fifty or sixty patient studies (also known as panels), each comprising eight film-screens of the eight views described above, and the average mammographer can usually review a patient study in approximately one to two minutes. Although film-screen mammograms have drastically improved the ability of mammographers to detect the early signs of breast cancer, its accuracy can be improved.

Along with the other modalities for medical imaging, mammography is being propelled into the next century by progress in digital technology. Digital mammography may fundamentally change the practice of medicine, allowing the earliest signs of cancer to be detected more accurately, thereby dramatically improving patient outcomes. Specific advantages of digital mammography include the potential for better image quality, real-time display, image-enhancement capabilities, computer-assisted abnormality detection, and ease of image management and transfer (for remote interpretation). With respect to image enhancement, techniques are already known in the art for enhancing visualization of masses, microcalcifications, architectural distortions, and tissue densities.

Prototype full-breast detector systems are now available for acquiring mammograms digitally so that the images are never recorded on film. Similar systems are available for digitizing radiographs, including mammograms, from films or slides. It is presently unclear, however, how high resolution, full field of view (FOV) digital mammograms will be read. Suggested approaches include printing the digital images on laser film for viewing, the development of monitors having 4k×4k or greater pixel matrices, and use of head-mounted displays currently under development by the intelligence and defense community. Given the cost consciousness in the healthcare community, however, these approaches may be cost prohibitive or provide for insufficient radiologist productivity. Printing processed digital images on laser film merely compounds the high cost of film-screen radiographs with the high cost of digital receptor systems. Similarly, the high cost of monitors having 4k×4k pixel resolution, or head-mounted displays, can hardly be estimated at present, as such systems will be commercially unavailable for many years to come. Although digital workstations employing high definition ("HD") monitors with 1k×1k, or 2k×2k, pixel matrices have been proposed, a separate monitor is required for displaying each image in a patient study, again at a prohibitively high cost. In the case of digital mammography, a total of eight or more HD monitors would be required.

Another important issue overlooked in discussions of the future of digital mammography is how the digital workstations can permit the mammographer to navigate through a mammographic study efficiently. The various proposed approaches focus on displaying one radiographic image at a time on an HD monitor. Little if any attention has been given to how the radiologist will navigate through the images in a typical patient study, including possibly many renditions of each individual image, in an efficient manner so as to make the most cost-effective use of the radiologist's time. Continuing to overlook this issue will likely hinder the clinical acceptance of digital mammography.

What is needed is a system and method for viewing digitally acquired radiographs without requiring presently unavailable, high cost, HD monitors having 4k×4k or greater pixel matrices, and at speeds that make effective use of radiologists' time. Such a system and method would preferably allow a radiologist to view images on only one currently available HD monitor (i.e., having a 1k×1k or 2k×2k pixel matrix), or two at most, so as to minimize system costs. The radiologist should be able to use such a system and method in an intuitive manner so that only minimal training would be necessary. Minimizing the cost and the complexity of use of such a system, while maximizing the speed at which the images can be viewed, would facilitate its clinical acceptance, thereby promoting the progress of digital radiography and its corresponding medical advantages.

SUMMARY OF THE INVENTION

The inventor hereof has succeeded at solving these and other needs by designing and developing a navigation and display system, and a corresponding method, for viewing digitally acquired radiographs using only a single HD monitor in a first embodiment, or only two HD monitors in a second embodiment. The system is configured such that a radiologist can navigate his way through the multiple images of a typical patient study (as well as various renditions thereof) in an intuitive manner, as the radiologist selectively controls the display of the images on the HD monitor using hand movements analogous to the head and eye movements made by a radiologist when reviewing radiographs on filmscreens using a prior art multiviewer. Thus, the radiologist can be said to be trained as to how the inventor's system is used even before the radiologist is actually introduced to the system. Moreover, the system allows radiologists to review digitally acquired radiographs at speeds comparable to or greater than the speeds at which hard copy radiographs are typically reviewed. System costs are also controlled by use of only one or at most two HD monitors. Further, enabling efficient use of soft copy viewing helps to eliminate costs for film, film staging, film developing, and film storage, promotes remote viewing of images transmitted over digital networks, and allows the images to be stored on digital recording media.

The inventor's preferred system comprises a HD monitor for viewing digitally acquired images, a video buffer for storing the images to be displayed, and a control console having a graphical user interface (GUI) for controlling the display of the images on the HD monitor. By storing all of the images to be displayed for a patient study in the video buffer, the images can be selectively displayed in a seemingly instantaneous manner, as fetching of these images from disk are not required while the radiologist is reviewing the patient study. The video buffer can be of a size capable of storing more than two patient studies, or can instead be sized to store only two patient studies. In the latter case, the memory space used for storing the first patient, study can be overwritten after the first patient study is, reviewed, but while the second patient study is under review, so that a new, third patient study is available for review once the radiologist completes his review of the second patient study. Using this approach, the two memory spaces for storing two patient studies can be alternately updated such that a new patient study is always timely available for review by the radiologist.

The images to be displayed, which are stored in the video buffer, can include the radiographic images as originally captured, as well as various renditions thereof. Such renditions may include the original images as processed into different spatial resolutions, enhancements to the original images to highlight radiographic features of interest, or any combination thereof.

The GUI on the control console displays multiple icons, where each icon represents one of the radiographic images for the patient study in question. Thus, where a patient study routinely consists of, for example, eight images (such as four images from a current patient examination and four images from a prior examination), eight icons are displayed on the GUI. A cursor is also displayed on the GUI, and is coupled to a hand-held device, preferably a mouse. Movement of the mouse controls the location of the cursor with respect to the icons displayed on the GUI, which in turn controls the display of one or more of the images represented by the icons, or portions thereof, on the HD monitor. The icons can be custom generated from the original image data, or can be standard icons that are not changed from one patient study to another.

The icons are arranged on the GUI in the same fashion that the views which they represent are typically hung on a prior art multiviewer when hard copy display is performed. Thus, if a first standard view is typically hung on a multiviewer immediately next to a second standard view such that a radiologist looks at the first standard view, and then moves his head and eyes sideways to look at the second standard view, then icons representing these views are similarly arranged on the GUI one immediately next to the other. As a result, the hand movements made by the radiologist to control the display of the images on the HD monitor with the mouse are highly analogous to the head and eye movements that must be made to review these images on hard copy film. In this way, the method by which the system is used is intuitive to radiologists, so that only minimal, if any, training is required, and so the system can be used to review radiographic images at speeds equal to or greater than the speeds at which hard copy films are typically reviewed. The radiologist will seldom have to look at the GUI for orientation, and can instead focus his attention on the one or two HD monitors upon which the images are displayed.

The system of the preferred embodiment is capable of displaying three different renditions of each image, where each rendition has a different spatial resolution.

The three different resolutions include: low resolution where all of the views of a patient study can be simultaneously displayed on one, or at most two, HD monitors; medium resolution where at least one but less than all of the images of the patient study can be displayed on a single HD monitor; and high resolution where only a portion of one of the images can be displayed on a single HD monitor. In the high and medium resolution modes, the position of the cursor with respect to the icons on the GUI identifies the particular image being displayed on the HD monitor. When operating in the high resolution mode, a window is displayed on the GUI around a portion of one of the icons (and around the cursor) to identify the particular portion of the image that is being displayed on the high resolution monitor. Selecting any of the various resolutions is easily accomplished by clicking appropriate buttons on the mouse.

While the principal advantages and features of the present invention have been described above, a more thorough understanding of the invention may be attained by referring to the drawings and the detailed description of the preferred embodiments which follow.

DETAILED DESCRIPTION OF THE PREFERRED EMBODIMENTS

Figure 2:
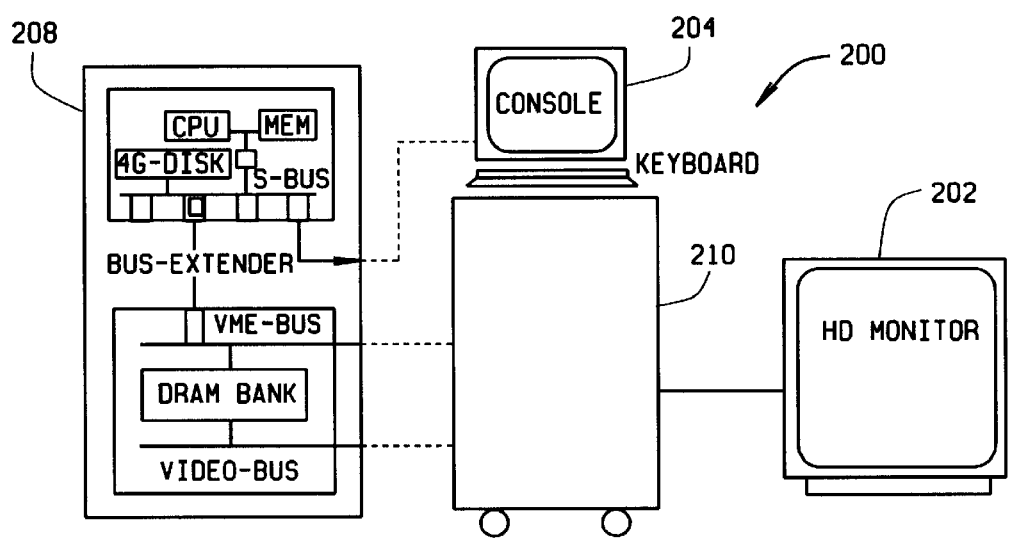
FIG. 2 is a block diagram of a navigation and display system according to a first embodiment of the present invention.

A first embodiment of a navigation and display system 200 according to the present invention is shown in FIG. 2 and includes a HD monitor 202, a control console 204, a UNIX workstation 208, and a video frame buffer 210 (i.e., dynamic video RAM). The UNIX workstation 208 controls the display of a graphical user interface (GUI) on the control console 204, and also provides instructions to the video frame buffer 210 to control the display of mammographic images, which are stored in the video frame buffer 210, on the HD monitor 202. A copy of the source programming code for the UNIX workstation 208 can be found in Appendix A in the parent application.

Figure 3:
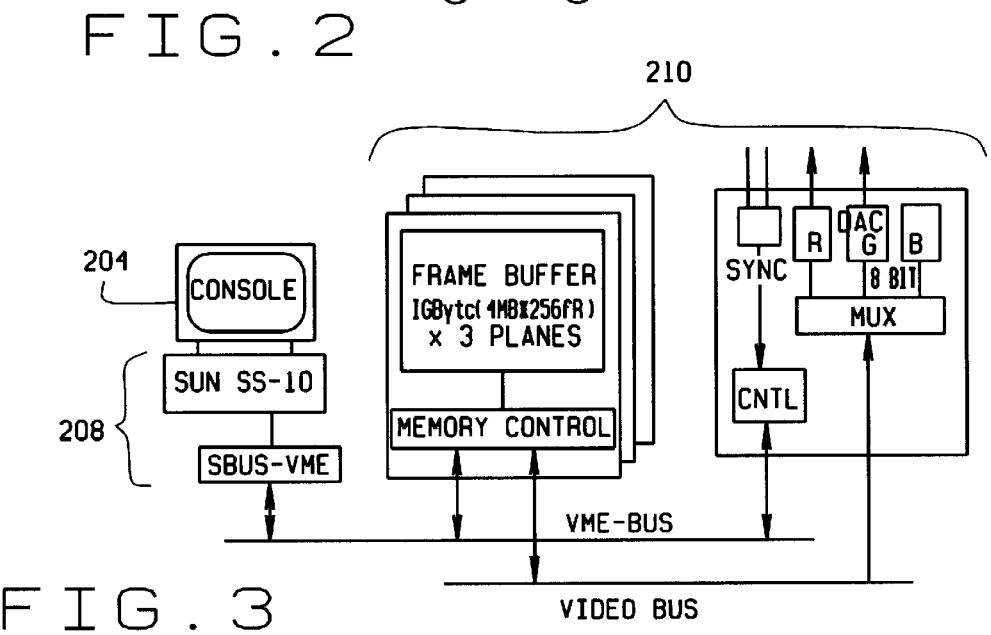
FIG. 3 is a more detailed block diagram of portions of the system shown in FIG. 2.

The video frame buffer 210 is configured to have a frame size of 4096×4096 pixels with a total of 64 frames that can be output at a rate of 60 frames/second. The video frame buffer 210 is preferably a Super FM-III designed by Nippon Telegraph and Telephone (NTT) of Japan. The UNIX workstation 208 is preferably a Sun Sparc Station-10. The control console 204 is a standard personal computer monitor for displaying the GUI that controls the display of images on the HD monitor 202, as described below. The HD monitor 202 is a Sony DDM-2801 color monitor having a 2048×2048 pixel matrix, where each pixel is driven by 8 bits of data. FIG. 3 illustrates the manner in which the UNIX workstation 208 selects a particular frame from the video frame buffer 210 for display.

The navigation and display system 200 of the first embodiment allows a radiologist to selectively and instantaneously display any one or all of the mammographic images for a particular patient study on the high resolution monitor 202, including the four images from the current examination and the four images from the prior examination. The images can be obtained by a digital receptor system having an array of approximately 4k×4k, 50 micron receptors, where each receptor has a 16 bit output, i.e., two bytes of data per receptor at 8 bits/byte. However, other receptor systems are currently under development, including those having a 12 bit output for each receptor, and those having an array of approximately 4k×5k receptors (50 microns or otherwise) and either a 12 or a 16 bit output for each receptor. The teachings of the present invention are equally applicable to these and other receptor systems.

As indicated, the receptor system used to collect the images displayed in the first embodiment generates 16 bits of data for each receptor, while the HD monitor 202 is configured for only 8 bits of data per pixel. In other words, the receptor system captures data at $2^{16}$ shades of gray, while the system 200 is capable of displaying only $2^8$ shades of gray. Ideally, a look-up table specific to the particular receptor system employed would be used to map each of the $2^{16}$ shades of gray into one of the $2^8$ shades of gray capable of display by the system 200. However, in the inventor's implementation of this embodiment, the second byte of data captured by each receptor was simply truncated for the sake of simplicity.

The high storage capacity of the video frame buffer 210 contributes significantly to the speed at which the mammographic images, and various renditions thereof, can be selectively displayed on the HD monitor 202, as no fetches from disk are required. Various renditions of the data acquired by the digital receptors can be generated and then stored in the video frame buffer 210 for selective and seemingly instantaneous display on the HD monitor 202. These renditions can include enhancements of the original mammographic images to highlight masses, microcalcifications, architectural distortions, and/or tissue densities, as is well-known in the art. In the first embodiment of the present invention, the renditions employed are of different spatial resolutions without any further enhancements. In particular, three renditions of each mammographic image were generated and/or stored in the video frame buffer 210 as approximately 4k×4k images, 2k×2k images, and 1k×1k images (referred to as 4k, 2k, and 1k renditions,, respectively), as explained further below. However, it should be understood that renditions of the images at any spatial resolution can equally be employed without departing from the scope of the invention.

As used herein, the term renditions includes the original mammographic images which were captured by the digital receptor system as approximately 4k×4k images and then stored in the video frame buffer 210 without modification.

The 2k renditions of the images can be generated by pixel averaging the 4k×4k array of data. The result is renditions of the original images that are similar to the images that would be obtained by a 2k×2k array of 100 micron receptors. Similarly, the 1k renditions of the images can also be generated by pixel averaging, resulting in renditions similar to the images that would be obtained by a 1k×1k array of 200 micron receptors. In this manner, renditions of the original images at differing spatial resolutions can be generated.

The mammographic images used in this embodiment of the invention were obtained by digitizing hard copy film into approximately a 4k×4k data array at 50 micron resolution. Thus, it should be understood that as used herein, the phrase "obtaining an image from a patient via a fixed number of digital receptors" includes digitizing radiographic images from film-screens previously produced for the patient. In addition, it should be noted that the images were obtained from film-screens of breast images that occupied less than fifty percent of the film-screens. The data acquired for the unused portions of the film-screens were simply discarded. The original images are therefore 2k×4k images, rather than 4k×4k images, the 2k renditions of the original images are essentially 1k×2k images, and the 1k renditions of the original images are essentially 500×1k images. Consequently, when the system is displaying the 1k renditions (also known as operating in the 1k mode), all eight of the mammographic images for a patient study can be simultaneously displayed on the HD monitor 202, which has a 2k×2k pixel matrix. Where such cropping is impractical or cannot be performed, all eight images of the patient study can alternatively be displayed on the HD monitor 202 (without cropping) at a lower spatial resolution, or can instead be displayed using two HD monitors, as described further below.

As indicated above, three different renditions of each of the eight mammographic-images in a patient study (including the renditions of the original images in unaltered form) are simultaneously held within the video frame buffer 210 for selective display on the HD monitor 202. As all 24 of these images (three renditions of each image times eight images) are not and cannot be simultaneously displayed on the HD monitor 202, the control console 204 is provided with the GUI to provide orientation to the radiologist as to where the images displayed on the monitor 202 are located in the memory space of the video frame buffer 210. As further explained below, the manner in which the system is operated is intuitive to radiologists such that the GUI will seldom be needed. Thus, the GUI can be thought of as a seldom used road map. Just as a road map is only needed the first few times one travels from point A to point B, or if one is lost, the GUI is only needed the first few times a radiologist uses the system 200, or if the radiologist becomes confused as to which image(s) are being displayed on the HD monitor 202. For this reason, the GUI provided on the control console 204 is not strictly necessary to implement the teachings of the present invention.

The preferred video frame buffer 210 is capable of holding a total of thirty-two patient studies, where each patient study includes the 4k, 2k, and 1k renditions of each of the eight mammographic images. These thirty-two patient studies can be loaded into the video frame buffer in approximately fifteen minutes (i.e., in less than thirty seconds per patient study). However, such a large video frame buffer is not essential to practicing the invention. A video frame buffer can instead be used that has enough memory to hold only two patient studies, including any desired number of renditions of each of the eight images in each patient study.

Where this alternative video frame buffer is employed, the memory space storing the first patient study can be overwritten (after the first patient study has been reviewed) by a third patient study during the time required for the radiologist to review the second patient study (i.e., preferably in less than one minute). Similarly, when the radiologist reviews the third patient study, the memory space storing the second patient study can be overwritten by a fourth patient study. In this manner, the memory spaces sufficient for storing only two patient studies can be alternately overwritten such that a new patient study is always available for review by the radiologist.

The GUI provided on the control console 204 includes icons which represent the mammographic views obtained for the current and prior examinations of the patient. Just as the films for the current and prior examinations were displayed on the lower level 102 and upper level 112, respectively, of the prior art multiviewer shown in FIG. 1, icons provided on a lower level of the GUI represent the four images of the current examination while icons provided on an upper level of the GUI represent the four images of the prior examination. The icons are preferably generated from the original mammographic images (or from one of the renditions thereof) in the same manner as were the 2k and 1k renditions (i.e., using pixel averaging to collapse the original data both spatially and in gray scale) so the icons closely resemble the images displayed on the HD monitor 102. The icons are preferably stored in the video RAM of the UNIX workstation 208 for display on the control console 204 when their corresponding patient study is loaded. Alternatively, the icons can be standardized, rather than generated from the actual mammographic images, so that the same icons are repeatedly used for each patient study.

A three-button mouse is provided to control an arrow (i.e., a cursor) displayed on the GUI, where the position of the arrow on the GUI controls the image(s) displayed on the HD monitor 202. When a patient study is first loaded, the system 200 is set to display the mammographic images on the HD monitor in the 1k mode (i.e., the default mode). Clicking the left mouse button causes the system to switch into the next higher resolution mode, such as the 2k or 4k mode. Clicking the middle mouse button causes the system to switch into the next lower resolution mode, such as the 2k or 1k mode. Clicking on the right mouse button brings up the next patient study that is held in the video frame buffer 210.

Figure 4:
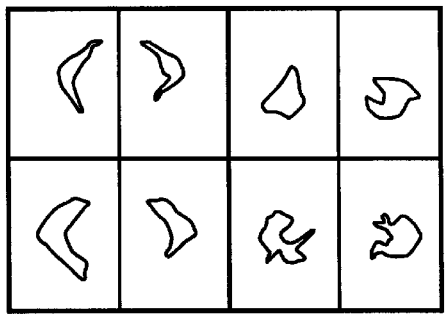
FIG. 4 illustrates the display of eight customized icons on the graphical user interface (GUI) of the control console.
Figure 5:
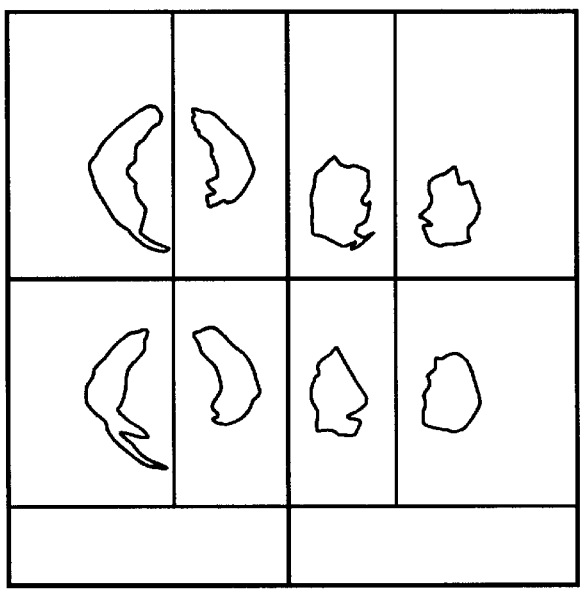
FIG. 5 illustrates the display of the eight standard images of a patient study on the HD monitor with the system in the 1k display mode.

Display of the GUI on the control console 204 is illustrated in FIG. 4. Two icons representing the new cc views (i.e., left and right) are positioned in a lower left quadrant of the GUI, two icons representing the old cc views are positioned in an upper left quadrant of the GUI, two icons representing the new oblique views are positioned in a lower right quadrant of the GUI, and two icons representing the old oblique views are positioned in an upper right quadrant of the GUI. Each of these four sets of icons are enclosed in boxes, where each box includes a vertical line separating the respective left and right icons as can be seen in FIG. 4. With the system 200 in the 1k default mode, all eight of the mammographic images are displayed on the HD monitor at 200 micron resolution, as shown in FIG. 5.

Figure 6:
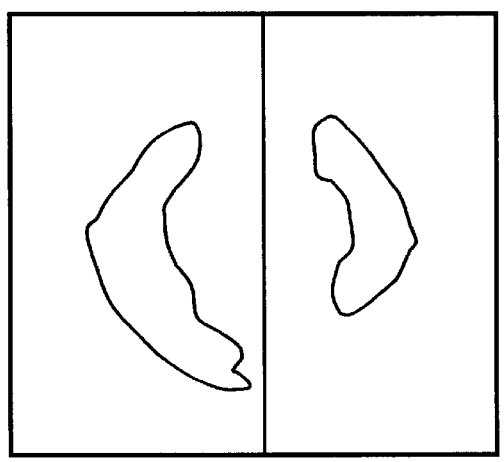
FIG. 6 illustrates the display of the cc views from the current examination on the HD monitor with the system in the 2k display mode.
Figure 7:
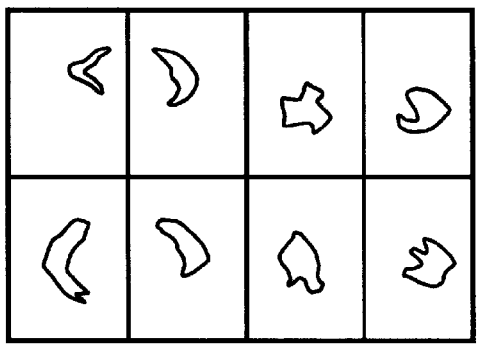
FIG. 7 illustrates the graphical user interface with the arrow positioned on the icon for the right cc view of the prior examination.
Figure 8:
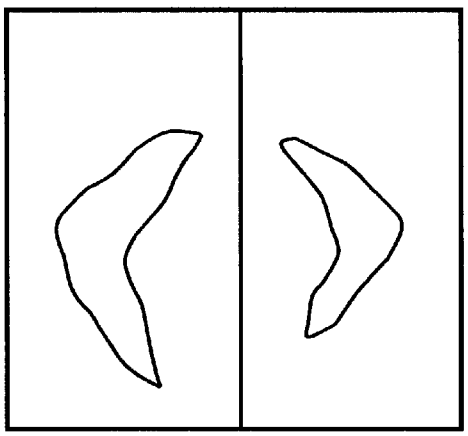
FIG. 8 illustrates the display of the cc images from the prior examination on the HD monitor with the system in the 2k display mode.

If the arrow is initially displayed near the top center region of the GUI, then when the system operator (i.e., a radiologist) moves the mouse towards him and to the left, the arrow on the GUI moves into the box enclosing the new cc views, as shown in FIG. 4. In the 1k mode, the position of the arrow relative to the icons has no bearing on the images displayed on the HD monitor 202. However, clicking on the left mouse button switches the system into the 2k display mode, and with the arrow positioned as shown in FIG. 4, the new cc views will be displayed on the HD monitor 202 at 100 micron resolution, as shown in FIG. 6. When the radiologist moves the mouse away from himself, the cursor on the GUI moves from the box enclosing the new cc views into the box enclosing, the old cc views, as shown in FIG. 7. Consequently, the cc views of the prior examination are displayed on the HD monitor 202 at 100 micron resolution, as shown in FIG. 8.

Figure 1:
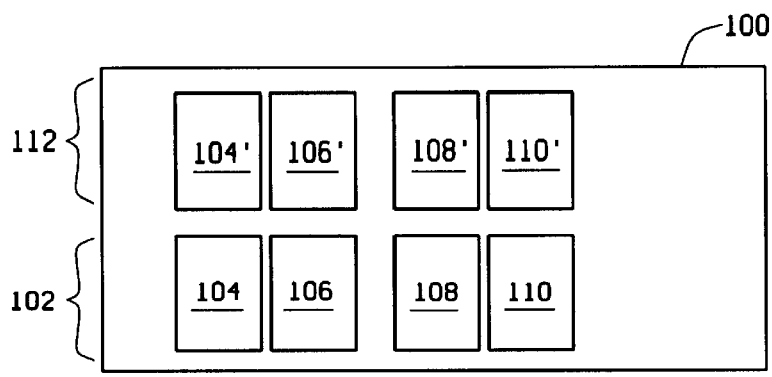
FIG. 1 is a schematic illustrating a prior art multiviewer displaying the eight standard views in a typical mammographic patient study.

By moving the mouse towards and away from himself, the radiologist can toggle the image displayed on the monitor 202 between the new cc views (FIG. 6) and the prior cc views (FIG. 8) at 100 micron resolution. These hand movements by the radiologist correspond to the head and eye movements previously performed by the radiologist when comparing the new cc views 104, 106 with the old cc views 104', 106' on hard copy film as shown in FIG. 1.

Figure 9:
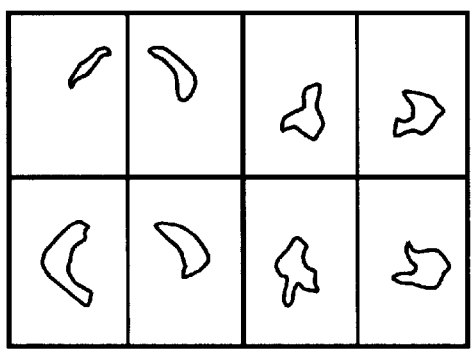
FIG. 9 illustrates the graphical user interface with the arrow on the icon for the right oblique view of the current examination.
Figure 10:
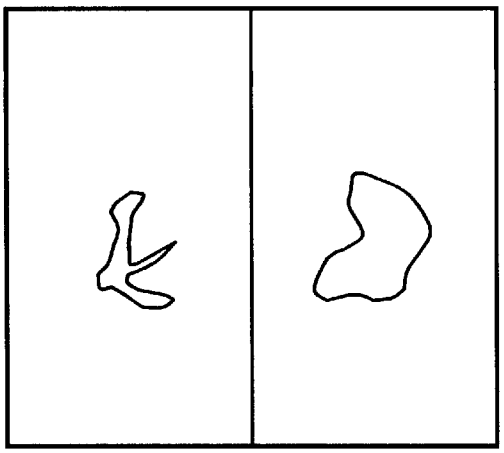
FIG. 10 illustrates the display of the oblique images from the current examination on the HD monitor with the system in the 2k display mode.
Figure 11:
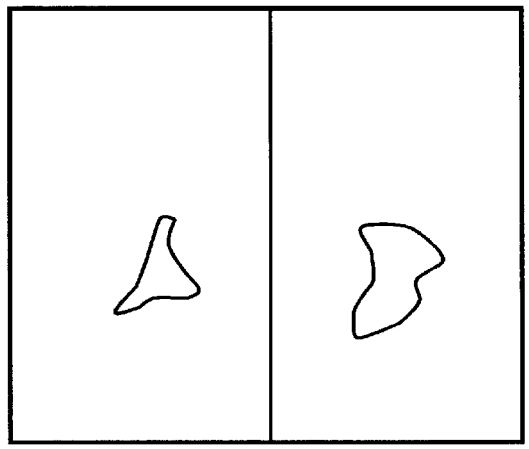
FIG. 11 illustrates the display of the oblique views from the prior examination on the HD monitor with the system in the 2k display mode.

With the system still in the 2k display mode, the radiologist can move his hand from left to right to move the arrow on the GUI from the box enclosing the new cc views into the box enclosing the new oblique views as shown in FIG. 9, thereby causing the left and right oblique views from the current examination to be displayed on the monitor 202 at 100 micron resolution, as shown in FIG. 10. Moving the mouse away from the radiologist causes the arrow on the GUI to move into thus box enclosing the old oblique views, thereby calling up the left and right oblique views from the prior examination on the monitor 202 at 100 micron resolution, as shown in FIG. 11.

Figure 12:
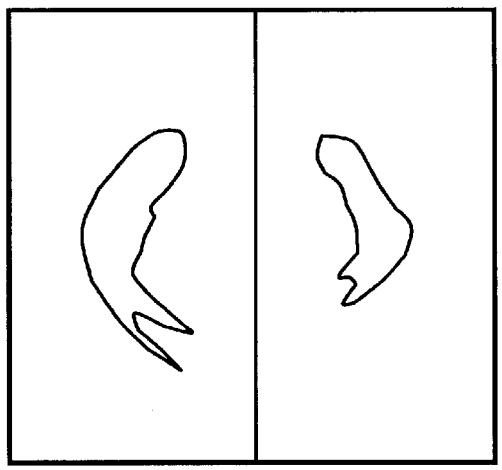
FIG. 12 illustrates the display of the cc views from the current examination on the HD monitor with the system in the 2k display mode, where a suspicious mass is visible.
Figure 13:
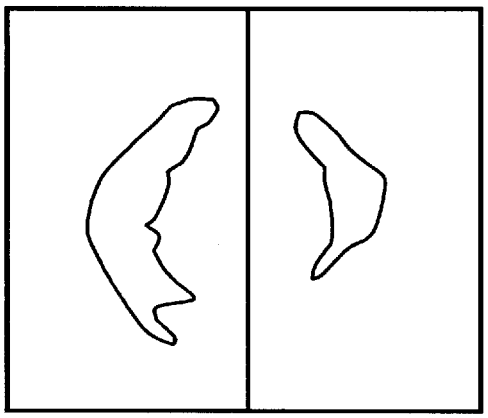
FIG. 13 illustrates the display of the cc views from the prior examination on the HD monitor with the system in the 2k display mode, where the suspicious mass shown in FIG. 12 is not visible.

FIGS. 12 and 13 are similar to FIGS. 6 and 3 as they illustrate the display of current and prior cc views, respectively, at 100 micron resolution. However, in FIG. 12 a mass can be seen in the right cc view of the current examination which is not evident in the right cc view of the prior examination shown in FIG. 13.

Figure 14:
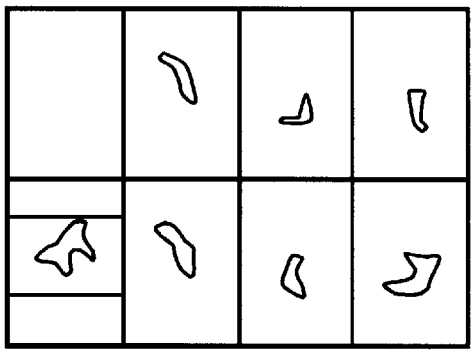
FIG. 14 illustrates the graphical user interface with a window enclosing a center portion of the icon for the right cc image from the current examination with the system in the 4W display mode.
Figure 15:
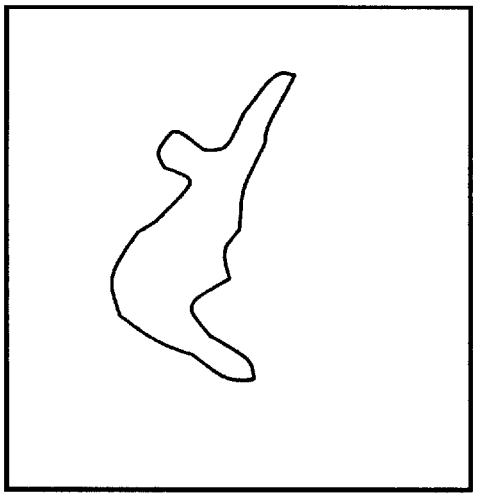
FIG. 15 illustrates a portion of the cc image from the current examination displayed on the HD monitor and corresponding to the portion of the icon enclosed on the GUI in FIG. 14 with the system in the 4k display mode.

Clicking again on the left mouse button switches the system into the next high resolution mode, i.e, the 4k mode. With the arrow on the GUI positioned in the center of the icon for the right cc view of the current examination, as shown in FIG. 14, a window is displayed within the box enclosing the new cc views. The window on the GUI indicates the portion of the right cc view of the; current examination that is displayed on the HD monitor 202 at 50 micron resolution, which is shown in FIG. 15.

Although not shown in the figures, moving the cursor to the top portion of the icon for the right cc view of the current examination causes the window to move up and enclose approximately the top half of the icon for the right cc image of the current examination. This, in turn, causes the enclosed portion of the right cc image to be displayed on the HD monitor 202 at 50 micron resolution. Thus, for each of the eight icons, there are three positions for the window displayed on the GUI when the system is in the 4k mode: the top half of the icon, the middle of the icon, and the bottom half of the icon. Note that portions of the image displayed with the window positioned, for example, on the bottom half of the icon are also displayed when the window is positioned about the center of the icon. In other words, the center position for the window overlaps with the top and bottom positions of the window so that features of the displayed image that are located at the boundary of one window position are not similarly positioned at the boundary of a different window position. Thus, the radiologist is less likely to overlook such features due to this overlapping approach to windowing.

Figure 16:
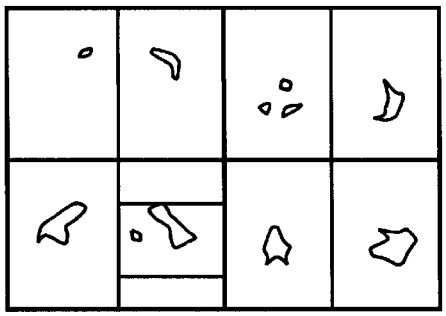
FIG. 16 illustrates the graphical user interface with a window enclosing a portion of the icon for the left cc image from the current examination with the system in the 4k display mode.
Figure 17:
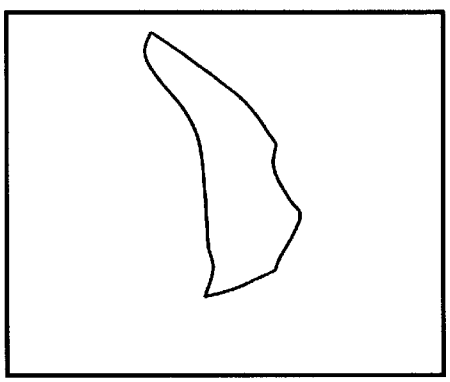
FIG. 17 illustrates the display of a portion of the left cc view from the current examination on the HD monitor which corresponds to the portion of the icon enclosed on the graphical user interface in FIG. 16 with the system in the 4k display mode.

Moving the mouse to the right causes the arrow on the GUI, and the window, to move from the center of the icon for the current right cc image to the center of the icon for the current left cc image, as shown in FIG. 16. As a result, the corresponding portions of the image enclosed by the window are displayed on the HD monitor at 50 microns resolution, as shown in FIG. 17. In this manner, any portion of any of the eight mammographic images of a patient study can be displayed on the HD monitor at 50 micron resolution. Note that microcalcifications that were not visible in the current left cc image at 100 micron resolution, shown in FIG. 6, are visible in FIG. 17 due to the higher resolution of the displayed image.

As an alternative to windowing when the system is in the 4k display mode, scrolling of the image (horizontally, vertically, or both) can be implemented. For example, the system can display a 2k×2k image on the HD monitor at 50 micron resolution, where the center of the displayed image corresponds to the position of the arrow on one of the icons. However, where scrolling is performed, the system is preferably configured to ignore slight movements of the mouse so as to stabilize the image displayed on the HD monitor, as an unstable image is distracting for the system operator.

It should again be noted that movements of the mouse towards and away from the radiologist, and from left to right, correspond to head and eye movements which are made by radiologists when reviewing mammographic images on the multiviewer 100 shown in FIG. 1. Thus, the manner in which a radiologist utilizes the mouse to navigate his way through the various mammographic images is intuitive, as the hand movements substantially correspond to the head and eye movements employed when reviewing mammographic images on hard copy film. For these reasons, once the radiologist learns how to zoom in and out on the displayed images by simply clicking on the left and center mouse buttons, and learns to load the next patient study by simply clicking the right mouse button, the radiologist can quickly become accustomed to the system with minimal training. In other words, the system 200 of the present invention is highly user friendly. Due to this intuitive manner in which the radiologist can quickly navigate through the mammographic images, there quickly becomes little if any need for the radiologist to look at the GUI. Instead, the radiologist can concentrate his attention on the HD monitor, thereby increasing the speed, and hence the efficiency, of mammographic studies.

The speed at which soft copy viewing can be performed is also dramatically enhanced by storing all of the images and their several renditions in the video frame buffer for display upon operator command. Further still, the system 200 of the present invention is not only intuitive and easy to learn, but is also significantly less expensive than systems employing a HD monitor for each mammographic image to be displayed.

While the preferred hand-operated device for controlling the display of the mammographic images is a mouse, it should be understood that a large number of alternative devices exist for performing this function. Some examples of these alternatives include track balls, touch screens, touch pads, electronic gloves (i.e., virtual motion gloves), joy sticks, light pens, manual electronic buttons or switches, and even keyboards, where the arrows on the keyboard can be used for controlling the images displayed.

In this embodiment, where the three renditions of the digitally acquired mammograms were not enhanced to highlight mammographic features of interest, the 4k display mode was necessary primarily for identifying clustered microcalcifications. It should be understood, however, that where the various renditions include enhancements to the mammographic images to highlight features of interest, there may be little if any need for high resolution display of the images, and the 2k and 4k display modes might be eliminated.

Figure 18:
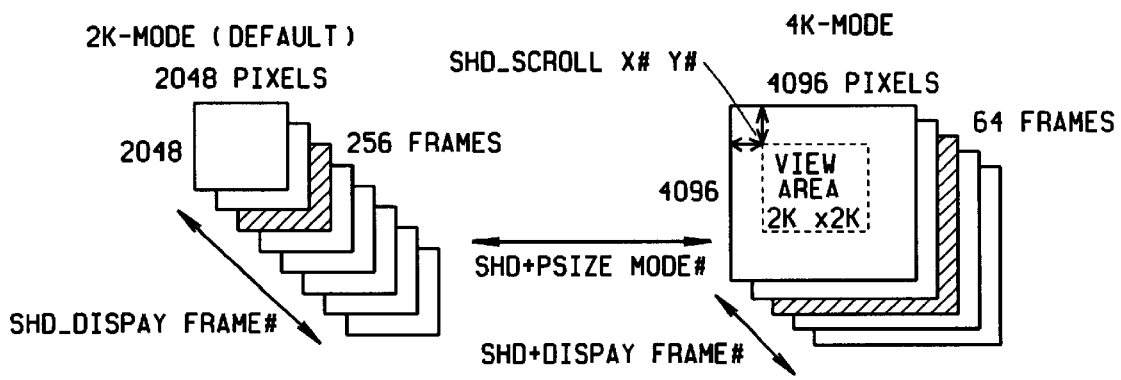
FIG. 18 is a diagram illustrating the manner in which the video frames for the video frame buffer are reconfigured from 2k×2k pixels to 4k×4k pixels.
Figure 19:
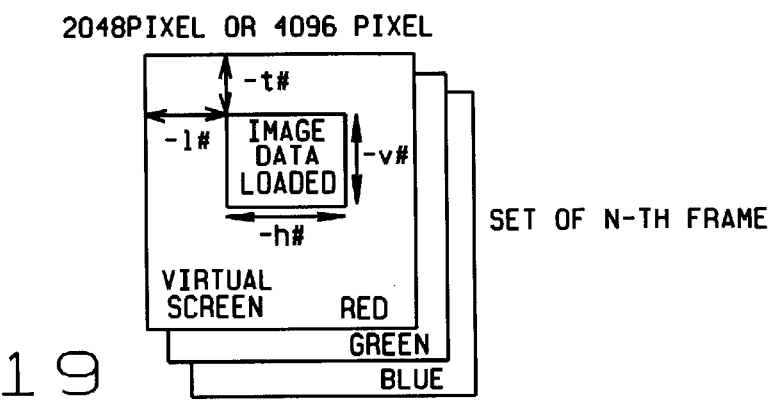
FIG. 19 is a diagram illustrating the manner in which the mammographic images are loaded into the video frames of the video frame buffer.
Figure 20:
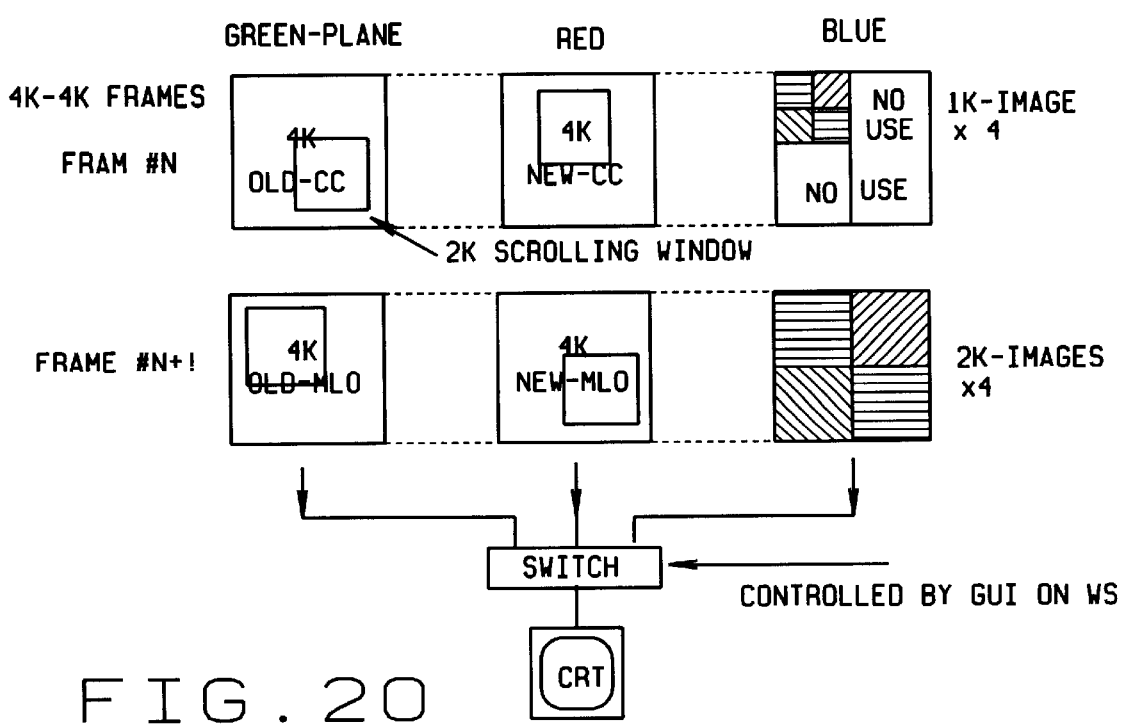
FIG. 20 is a diagram illustrating the manner in which the video frame buffer is configured for outputting the 1k, 2k and 4k images to a single high definition monitor using RGB channels.

The video frame buffer described above was originally configured to drive a monitor having 2048×2048 pixels with 256 video frames. FIG. 18 illustrates the manner in which this video frame buffer was reconfigured, as known in the art, to drive a monitor having 4096×4096 pixels with 64 video frames. FIG. 19 illustrates how the image data is loaded into the video frame buffer. FIG. 20 illustrates the manner in which the video frame buffer, which was originally configured to drive a color monitor, was reconfigured to output the 1k, 2k and 4k images using the blue, red and green channels, respectively, and a switch for selecting one of these channels for driving the HD monitor. The RGB inputs on the color HD monitor were simply tied together and connected to the switch shown in FIG. 20.

With reference to the source programming code provided in Appendix A, the video buffer call function shd_psize (shd_cmd_psize) is used to set the size of the video frames to 4k×4k pixels, as can be seen in FIG. 18. The call function shd_disp(shd_cmd_display) is used to select a particular frame within the video buffer for display. The call function shd_scroll(shd_cmd_scroll) is used to specify the 2k×2k portion of the selected frames that is to be displayed when windowing is performed in the 4k display mode.

As mentioned above, the original mammographic images utilized in the first embodiment were cropped to permit simultaneous display of all eight images of a patient study on the HD monitor 202 with the system in the 1k display mode. Where such cropping is impractical or otherwise unworkable, but simultaneous display of 1k renditions of all eight images in a patient study is desirable, an additional monitor identical to the HD monitor 202 (i.e., having a 2k×2k pixel matrix) can be provided. In this alternative embodiment, using the GUI to load a patient study would result in the display of the eight icons on the GUI in the same manner as described above, but with the cc views from the current and prior examinations displayed on the first HD monitor at 200 micron resolution, while the oblique views from the current and prior examinations are displayed on the second HD monitor, also at 200 micron resolution.

Thereafter, clicking the left mouse button to switch the system into the 2k display mode, and with the arrow on the GUI positioned within, for example, the box enclosing the cc views from the current examination, the right cc view of the current examination is displayed on the first HD monitor, while the left cc view of the current examination is displayed on the second HD monitor, both at 100 micron resolution. Moving the arrow on the GUI into the box enclosing, for example, the oblique views from the prior examination would similarly result in the display of the right oblique view from the prior examination on the first HD monitor at 100 micron resolution, while the left oblique view from the prior examination is displayed on the second HD monitor, also at 100 micron resolution.

Clicking the left mouse button again to switch the system into the 4k display mode causes a window to appear on the GUI which circumscribes the arrow and a 2k×2k portion of an icon from the current examination which will be displayed on the first HD monitor. At this time, the second HD monitor displays a corresponding portion of that same image, but from the prior examination. In this embodiment, there are nine potential positions of the window (rather than just three as in the previous embodiment); three window positions for the left side of each of the eight icons, three window positions for the center, and three window positions for the right side.

Figure 21:
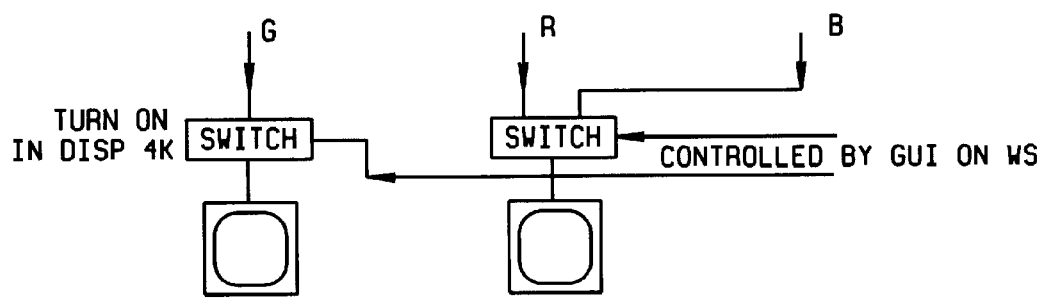
FIG. 21 is a diagram illustrating an alternative embodiment where the video frame buffer is configured for outputting the 1k, 2k and 4k images to two high definition monitors using RGB channels.

The source programming code for an embodiment utilizing two HD monitors is attached as Appendix B in the parent application. FIG. 21 illustrates the manner in which the RGB channels of the video frame buffer, which were reconfigured as described above with reference to FIG. 20, are provided to two HD monitors via two switches under-the control of the software provided in said Appendix B.

While the preferred embodiment of the present invention relates to digital mammography, it is well-known that mammography requires greater image resolution than any other imaging modality of radiology. Accordingly, the teachings of the present invention can be readily applied to any of these other modalities, including CT scans, chest imaging, bone imaging, and MRI.

As used herein, the phrase "high resolution digitized images" refers to images originally acquired (i.e., prior to processing) at resolutions greater than the pixel resolution of a monitor upon which the images will be displayed.

There are various changes and modifications which may be made to the invention as would be apparent to those skilled in the art. However, these changes or modifications are included in the teaching of the disclosure, and it is intended that the invention be limited only by the scope of the claims appended hereto, and their equivalents.

What is claimed is:

1. A method for rapidly selecting and displaying multiple, separate radiologic images on a computer system having a monitor by selectively controlling the transfer of images from a computer memory to the monitor using hand movements substantially corresponding to head and eye movements employed by a user when viewing the multiple separate images on hard copy film as viewed on a multiviewer, the method including selectively displaying the multiple images on the monitor, the images being multiple, separate images acquired from at least one radiologic examination of a specific patient displaying the images in a defined pattern on the monitor corresponding to the accepted radiologic format in which the images are displayed on the multiviewer, and navigating between images displayed on the monitor by using hand movements to control an input device to recall images from computer memory in a pattern that is the same as said defined, with the pattern which the use would use head and eye movements to navigate between the hardcopy films displayed on the multiviewer, the images or portions of the images being selectively available in at least one rendition with the method facilitating navigation through the images regardless of the number of renditions displayed.

2. The method of claim 1 wherein the method includes displaying images in rows and columns on the monitor, each row comprising images from a single examination of a patient, and each column comprising corresponding images of a particular view from separate examinations of the patient.

3. The method of claim 1 wherein the monitor is a high definition monitor.

4. The method of claim 1 wherein the images include sections of digital radiologic images wherein the pixel area of the digital radiologic images is greater than that of the monitor.

5. The method of claim 4 wherein the multiple radiologic images comprise a plurality of renditions for each image originally acquired from a patient, and the method further includes selecting an operating mode for said system to thereby select a particular set of renditions to display.

6. The method of claim 1 wherein the method further includes selecting the resolution of the images displayed.

7. The method of claim 1 wherein the computer system is capable of transferring a high resolution, digital image from memory to the monitor substantially instantaneously.

8. The method of claim 7 wherein the computer system uses a video buffer with memory of sufficient size to store and to transfer substantially instantaneously the radiologic images for at least one patient study to the monitor.

9. The method of claim 1 wherein the computer system further includes a second monitor having a graphical user interface, the user interacting with the graphical user interface by hand movements substantially corresponding to head and eye movements employed by a user when viewing the multiple, separate images on hard copy film as viewed on a multi-viewer.

10. The method of claim 9 wherein the computer system further includes at least one additional monitor, and the method further includes selectively controlling the display of the images on the at least one additional monitor also using hand movements substantially corresponding to head and eye movements employed by a user when viewing the multiple separate images on hard copy film.

11. The method of claim 10 wherein the at least one additional monitor is a high definition monitor.

12. A method for rapidly selecting and displaying multiple, separate radiologic images on a computer system having a monitor by selectively controlling the transfer of images from a computer memory to the monitor using hand movements substantially corresponding to head and eye movements employed by a user when viewing the multiple, separate images on hard copy film as viewed on a multi-viewer, the method including selectively displaying the multiple images on the monitor, the images being multiple, separate images acquired from at least one radiologic examination of a specific patient, displaying the images in a defined pattern on the monitor corresponding to the accepted radiologic format in which the images are displayed on the multiviewer, and navigating between the images displayed on the monitor by selecting at least a portion of an icon using hand movements in a manner corresponding to that by which the user would navigate between the hard copy film displayed on the multiviewer using head and eye movement, the images being selectively available in different degrees of resolution with the method facilitating navigation through the images regardless of the degree of resolution of the image displayed.

* * * * *

UNITED STATES PATENT AND TRADEMARK OFFICE
CERTIFICATE OF CORRECTION

PATENT NO. : 6,243,095 B1
DATED : June 5, 2001
INVENTOR(S) : Shile et al.

It is certified that error appears in the above-identified patent and that said Letters Patent is hereby corrected as shown below:

Column 5,
Line 21, replace "4W" with -- 4K --

Column 9,
Line 30, replace "3" with -- 8 --

Column 12,
Line 45, replace "use" with -- user --

Signed and Sealed this

Twenty-sixth Day of February, 2002

Attest:

JAMES E. ROGAN
Attesting Officer
Director of the United States Patent and Trademark Office